United States Patent [19]
Dorn et al.

[11] Patent Number: 5,635,194
[45] Date of Patent: Jun. 3, 1997

[54] DETERGENT RANGE ETHOXYLATED ALCOHOLS TO CONTROL BLACK FLIES

[75] Inventors: Philip B. Dorn, Katy, Tex.; John H. Rodgers, Jr., Oxford, Miss.

[73] Assignee: Shell Oil Company, Houston, Tex.

[21] Appl. No.: 513,064

[22] Filed: Aug. 9, 1995

Related U.S. Application Data

[63] Continuation of Ser. No. 153,592, Nov. 12, 1993, abandoned.

[51] Int. Cl.$^6$ .................................................. A01N 25/28
[52] U.S. Cl. ........................... 424/405; 424/408; 424/489; 514/723
[58] Field of Search .......................... 424/450, 489, 424/405, 408; 514/723

[56] References Cited

U.S. PATENT DOCUMENTS

| | | | |
|---|---|---|---|
| 3,429,827 | 2/1969 | Ruus | 252/316 |
| 4,160,033 | 7/1979 | Garrett et al. | 424/285 |
| 4,424,642 | 1/1984 | Stubler et al. | 43/114 |
| 4,470,966 | 9/1984 | Cormier | 424/330 |
| 4,474,678 | 10/1984 | Lutz et al. | 252/174.21 |
| 4,484,007 | 11/1984 | Cardenas et al. | 568/268 |
| 4,623,540 | 11/1986 | Costanza et al. | 424/81 |
| 4,705,900 | 11/1987 | Whittle | 568/367 |
| 4,816,256 | 3/1989 | Randen | 424/405 |
| 4,818,534 | 4/1989 | Levy | 424/404 |
| 4,822,613 | 4/1989 | Rodero | 424/405 |
| 4,853,223 | 8/1989 | Graf et al. | 424/405 |
| 4,889,710 | 12/1989 | Hagarty | 424/45 |
| 4,983,390 | 1/1991 | Levy | 424/404 |
| 4,985,251 | 1/1991 | Levy | 424/404 |
| 5,037,653 | 8/1991 | Dawson | 424/405 |
| 5,078,782 | 1/1992 | Nielsen et al. | 71/100 |
| 5,094,853 | 3/1992 | Hagarty | 424/405 |
| 5,116,618 | 5/1992 | Hagarty | 424/405 |
| 5,145,604 | 9/1992 | Neumiller | 252/312 |
| 5,164,096 | 11/1992 | Nunn | 210/754 |
| 5,225,278 | 7/1993 | Kielbania, Jr. et al. | 428/402.22 |

*Primary Examiner*—Neil S. Levy
*Attorney, Agent, or Firm*—Donna K. Blalock; Y. Grace Tsang

[57] ABSTRACT

Populations of black flies can be controlled by introducing an effective amount of water soluble detergent range ethoxylated alcohols into the aquatic habitats where black fly larvae are found.

10 Claims, No Drawings

1

DETERGENT RANGE ETHOXYLATED ALCOHOLS TO CONTROL BLACK FLIES

This is a continuation of application Ser. No. 08/153,592, filed Nov. 12, 1993 now abandoned.

FIELD OF THE INVENTION

The present invention relates to an environmentally safe process for controlling black fly populations by introducing an effective amount of water soluble detergent range ethoxylated alcohols into the aquatic habitats where black fly larvae are found.

BACKGROUND OF THE INVENTION

The black fly (Simulidae) is an ubiquitous pest which inhabits a wide variety of aquatic habitats. These pests are a nuisance since they often bite livestock, poultry and man. They are known to transmit pathogens such as filarial nematodes, viruses and avian protozoan parasites.

Typically, the larvae of the black fly can be found in and around aquatic habitats such as fast and slow flowing streams, shallow ponds or standing water sources during certain times of the year. The larvae attach to various substrates in the aquatic habitat such as logs and rocks where after a period of time, they pupate and eventually hatch.

A variety of pesticides have been used to control black flies and other similar pests. While many of these pesticides are arguably effective, they exhibit undesirable environmental effects including toxicity to non-target aquatic species which renders them unacceptable for widespread use. Applicants have discovered a process for controlling the black fly population utilizing low aqueous concentrations of nonionic ethoxylated surfactants, specifically detergent range ethoxylated alcohols, which biodegrade rapidly to carbon dioxide and water thereby making them compatible with the environment.

Various processes for controlling an assortment of pests exist in which surfactants are utilized in combination with active pesticides for the control or elimination of such pests. The surfactants in these processes are not utilized as active pesticides but are instead utilized as diluents, carrier materials, adjuvants, foam causing ingredients, wetting agents, dispersing agents and emulsifying agents. See, for example, U.S. Pat. Nos. 4,623,540; 4,822,613; 5,037,653; 5,078,782; 4,470,966; 5,145,604; 4,853,223; 4,424,642; 4,889,710; 5,094,853; 5,116,618; 4,816,256; 4,818,534; 4,983,390; and 4,985,251 for patents in which surfactants are utilized. In addition, U.S. Pat. No. 4,160,033 describes a process in which a surfactant is utilized to affect surface tension by drowning mosquito larvae and pupae.

In the present process, it has been found that the particular ethoxylated surfactant utilized, a detergent range ethoxylated alcohol, acts as the sole active component for preventing black fly larvae from pupating and maturing. These ethoxylated surfactants provide pesticidal selectivity when used in the amounts specified without producing undesirable effects in mammals or aquatic species.

SUMMARY OF THE INVENTION

Black fly populations may be controlled by adding effective amounts of water-soluble ethoxylated surfactants of the general formula I:

wherein R is an alkyl group of from 8 to 18 carbon atoms and x has an average value from 4 to 10 to aquatic habitats where black fly larvae are found to prevent the larvae from pupating and maturing.

DESCRIPTION OF THE PREFERRED EMBODIMENTS

In the process of the present invention, it is possible to control black fly populations by utilizing effective amounts of water-soluble ethoxylated surfactants of the general formula I:

wherein R is an alkyl and x is an average value from about 4 to about 10. The —O—(CH$_2$—CH$_2$ O)$_x$—H group of formula I is hereinafter referred to as the ether substituent of the ethoxylated surfactant. Compounds having an alkyl group substituted by multiple ether substituents are generally not considered as ethoxylated surfactants for purposes of the present invention although those of ordinary skill in the art will recognize that in making ethoxylated surfactants such as those represented by formula I, small amounts of molecules having multiple ether substituents bound to a single alkyl group may result. In the process of the present invention, compounds having multiple ether substituents bound to a single alkyl group will preferably be present only in minimal amounts. Preferably no more than about two percent of the molecules utilized as ethoxylated surfactants in the present process will contain multiple ether substituents bound to a single alkyl group. Representative ethoxylated surfactants of formula I which are useful in the present invention include, but are not limited to those described in U.S. Pat. No. 4,474,678.

In many instances, the ethoxylated surfactants of formula I utilized will be represented by a variety of specific ethoxylated surfactants, differing one from the other with respect to the carbon number of the alkyl moiety (R) and/or the structure of the alkyl moiety (e.g., the nature and degree of branching in its carbon structure) and/or the ethylene oxide adduct number (i.e., the value of x in formula I) and/or the position of the carbon atom of the alkyl moiety to which the ether substituent is bound.

The ethoxylated surfactant of formula I suitably consists of ethoxylate molecules having an alkyl moiety (R) with an average carbon number from 8 to 18, inclusive. Preferably, the carbon number of the alkyl moiety will be from 9 to 16, inclusive. Particularly preferred ethoxylated surfactants for use in the present process include those having an alkyl moiety with 11 to 15 carbon atoms, inclusive, with the most preferred having from 14 to 15 carbon atoms, inclusive.

In terms of the number of ethylene oxide adducts (i.e., the value of the integer x in formula I), the ethoxylate components of the ethoxylated surfactants utilized in the present invention are suitably limited to mixtures of ethoxylate molecules for which the average adduct number (the average value of x) is from about 4 to about 10 (per mole of alcohol utilized in preparing the ethoxylated surfactants). Preference is given to those ethoxylated surfactants wherein x has an average value from about 5 to about 9. In the most preferred embodiment of the present invention, x has an average value of about 7.

The ethoxylated surfactants of formula I are generally preferred to be linear compounds in which the ether substituent is bound to a primary carbon atom of the alkyl chain (R) although ethoxylated surfactants in which the ether substituent is bound to a secondary carbon atom of the alkyl chain are also considered to be within the scope of this invention as well as any mixtures thereof. Ethoxylated surfactants in which branching occurs within the alkyl chain are also considered to be within the scope of the present invention although when branching occurs, it is generally of a limited nature. Typically, at least about 80% of the molecules in a given sample are linear.

The ethoxylated surfactants of formula I may be made by any conventional process known in the art including, but not limited to, the processes described in U.S. Pat. No. 4,474,678. Such processes typically consist of the sequential addition of ethylene oxide to the corresponding alkanol (ROH) in the presence of a catalyst. Select ethoxylated surfactants which may be used in the present process are also available commercially such as NEODOL 91-6, NEODOL 45-7, NEODOL 45-13, NEODOL 25-3, NEODOL 25-9, NEODOL 25-12 and NEODOL 1-5 (each available commercially from Shell Oil Company). While any ethoxylated surfactant of formula I may be utilized in the process of the present invention, the preferred commercially available ethoxylated surfactant is NEODOL 45-7.

The process of the present invention consists of adding an effective amount of the ethoxylated surfactant of formula I to aquatic habitats containing black fly larvae in order to prevent the larvae from pupating and maturing. The ethoxylated surfactants of the present invention are especially attractive when utilized at low concentrations since they have a high rate of degradation which makes them environmentally safe with regard to other life forms while controlling the black fly population. While the amount of ethoxylated surfactant utilized will normally depend upon the particular compound of formula I being utilized, the ethoxylated surfactant will typically be added to aquatic habitats in which black fly larvae are located in an amount less than about 200 ppb (parts per billion). Preferably, the amount will be from about 1 ppb to about 175 ppb, more preferably from about 75 ppb to about 150 ppb, even more preferably from about 85 ppb to 125 ppb and most preferably about 100 ppb.

The aquatic habitats of black fly larvae to which the ethoxylated surfactant of formula I is added comprises relatively shallow water sources such as fast and slow-flowing streams, shallow ponds or any area where standing water may be found. The larvae attach to various substrate in the aquatic habitat such as logs and rocks.

The ethoxylated surfactant is typically added to these aquatic habitats prior to the pupation of the black fly larvae, during the period of time in which the black fly larvae is developing which depends upon water temperature and latitude. For example, in the Southeastern United States, the ethoxylated surfactant should be added during the months of May and June. Since the larvae are in varying stages of development, it is necessary to administer the ethoxylated surfactants over the entire period in which the black fly larvae are developing for successful control.

The manner in which the ethoxylated surfactants are added to the aquatic habitat is not critical to the present invention provided that the method of delivery is sufficient to achieve the required dosage for the area or volume being treated. Conventional methods which allow relatively precise amounts of the ethoxylated surfactant to be delivered to aquatic habitats include, but are not limited to, methods such as microencapsulation and the use of time-release drip pumps.

Processes for the microencapsulation of active ingredients of different fields of action have long been known by those of skill in the art, for example, from U.S. Pat. Nos. 3,429,827, 5,225,278 and 5,164,096. Such processes may be utilized to distribute the ethoxylated surfactant of the present invention provided the material utilized to "encapsulate" the ethoxylated surfactant does not present an environmental threat. Such processes involve incorporating the active ingredient, in the present process the ethoxylated surfactant, into a media such as gum arabic or gelatin which will slowly release particular amounts of the ethoxylated surfactant into the aquatic habitat over a period of time. Such processes are advantageous since they all allow a one-time treatment which would last throughout the development of the larvae.

In addition, the ethoxylated surfactant may be delivered to the aquatic habitat by means of a time-release drip pump which dispenses select amounts of the ethoxylated surfactant into the aquatic habitat over a period of time thereby maintaining the necessary treatment concentration to prevent pupation and maturation of the black fly larvae. In order to adequately deliver the specific amount of ethoxylated surfactant utilizing such pumps, in many instances it will be necessary to dilute the ethoxylated surfactant in an inert carrier such as water. The pump will be equipped with a timing device and at specific intervals will deliver specific amounts of the neat or diluted ethoxylated surfactant into the aquatic habitat where the black fly larvae are found.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be further described by the following Illustrative Embodiment which is provided for illustrative purposes only and is not to be construed as limiting the invention.

ILLUSTRATIVE EMBODIMENT

Illustrative Embodiment 1

A set of eight experimental streams (6.87m L×0.58 m W×0.31 m D) providing a flow of 76.8 L/min at a velocity of 25 cm/s from virgin springs with constant water quality were constructed for use in determining the effects of NEODOL 45-7 on various life forms. NEODOL 45-7 was dosed at three nominal concentrations (100 ppb, 200 ppb and 400 ppb) using calibrated delivery pumps in six of the streams from stock solutions which were replaced weekly during the thirty day period of the experiment. The remaining two streams were not treated with NEODOL 45-7, but were instead maintained as control streams. Samples from designated locations within each steam were collected during the thirty day experiment and analyzed to determine surfactant concentration and surfactant structure. Measurement parameters in the streams were for individual species toxicity response in acute and chronic end points to plants, invertebrates and fish. Community measurements of chlorophyll a, phaeophytin, respiration, plant biomass were also studied. Invertebrate measurements of community response were species numbers, density and diversity. In addition, the number of drifting invertebrates was evaluated. The results (as indicated in Table 1) show the community measurement endpoints (in parts per billion) at which effects due to NEODOL 45-7 were noted.

TABLE 1

| Chlorophyll a | >550 ppb |
|---|---|
| periphyton | >550 ppb |
| pheophytin a | >550 ppb |

TABLE 1-continued

| | |
|---|---|
| cell leakage | >550 ppb |
| plant biomass | >550 ppb |
| invertebrate density | >330 ppb |
| invertebrate drift | >330 ppb |
| simulidae (black fly) density | 126 ppb |
| bluegill survival | >550 ppb |
| bluegill growth | >330 ppb |
| fathead survival | >330 ppb |
| fathead egg production | temperature too low for reproduction |
| fathead growth | >330 ppb |
| fathead larval survival | temperature too low for reproduction |

What is claimed is:

1. A process for controlling the population of black flies (Simulidae) which process consists essentially of introducing into an aquatic habitat containing black fly larvae an effective amount sufficient to prevent the larvae from entering pupation and maturing of a water-soluble ethoxylated surfactant of the formula I:

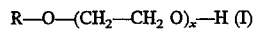

$$R-O-(CH_2-CH_2 O)_x-H \quad (I)$$

wherein R is a linear alkyl group of from 8 to 18 carbon atoms, x has an average value from about 4 to about 10 and the amount of water-soluble ethoxylated surfactant is less than about 200 ppb in the aquatic habitat.

2. The process of claim 1 wherein the amount of the water-soluble ethoxylated surfactant of formula I is from about 1 ppb to about 175 ppb in the aquatic habitat.

3. The process of claim 2 wherein R is from 9 to 16 carbon atoms and x is an average number from about 5 to about 9.

4. The process of claim 1 wherein the amount of the water-soluble ethoxylated surfactant of formula I is from about 75 ppb to about 150 ppb in the aquatic habitat.

5. The process of claim 4 wherein R is from 11 to 15 carbon atoms and x is an average number from about 5 to about 9.

6. The process of claim 5 wherein the water-soluble ethoxylated surfactant of formula I is introduced into the aquatic habitat by means of microencapsulation.

7. The process of claim 5 wherein the water-soluble ethoxylated surfactant is introduced into the aquatic habitat by means of a slow drip pump.

8. The process of claim 1 wherein R is from 14 to 15 carbon atoms and x is an average number of 7.

9. The process of claim 8 wherein the water-soluble ethoxylated surfactant of formula I is introduced into the aquatic habitat by means of microencapsulation.

10. The process of claim 8 wherein the water-soluble ethoxylated surfactant is introduced into the aquatic habitat by means of a slow drip pump.

* * * * *